US010478618B2

(12) United States Patent
Vilims

(10) Patent No.: US 10,478,618 B2
(45) Date of Patent: Nov. 19, 2019

(54) ADJUSTABLE LENGTH TENSION SLEEVE FOR ELECTRICAL OR THERMAL STIMULATION DEVICE

(71) Applicant: Bradley D. Vilims, Evergreen, CO (US)

(72) Inventor: Bradley D. Vilims, Evergreen, CO (US)

(*) Notice: Subject to any disclaimer, the term of this patent is extended or adjusted under 35 U.S.C. 154(b) by 16 days.

(21) Appl. No.: 15/794,663

(22) Filed: Oct. 26, 2017

(65) Prior Publication Data
US 2018/0085574 A1 Mar. 29, 2018

Related U.S. Application Data

(63) Continuation-in-part of application No. 14/639,671, filed on Mar. 5, 2015, now Pat. No. 9,802,037.

(51) Int. Cl.
A61N 1/08 (2006.01)
A61N 1/05 (2006.01)
A61N 1/40 (2006.01)

(52) U.S. Cl.
CPC ............ A61N 1/0551 (2013.01); A61N 1/08 (2013.01); A61N 1/086 (2017.08); A61N 1/403 (2013.01)

(58) Field of Classification Search
CPC ........ A61N 1/0551; A61N 1/08; A61N 1/086; A61N 1/403
See application file for complete search history.

(56) References Cited

U.S. PATENT DOCUMENTS

| 4,585,013 | A | * | 4/1986 | Harris .................. A61N 1/057 604/160 |
| 5,121,754 | A | | 6/1992 | Mullett |
| 5,341,806 | A | | 8/1994 | Gadsby et al. |
| 5,350,419 | A | | 9/1994 | Bendel et al. |
| 6,066,165 | A | | 5/2000 | Racz |
| 6,308,103 | B1 | | 10/2001 | Gielen |
| 6,516,227 | B1 | | 2/2003 | Meadows et al. |
| 6,740,446 | B2 | | 5/2004 | Corrigan et al. |
| 6,895,280 | B2 | | 5/2005 | Meadows et al. |
| 7,174,219 | B2 | | 2/2007 | Wahlstrand et al. |
| 7,177,702 | B2 | | 2/2007 | Wallace et al. |

(Continued)

FOREIGN PATENT DOCUMENTS

WO 2005102446 A1 11/2005

OTHER PUBLICATIONS

International Search Report and Written Opinion filed on May 17, 2016 in International Application No. PCT/US16/020363.

Primary Examiner — Amanda K Hulbert
Assistant Examiner — Natasha Patel
(74) Attorney, Agent, or Firm — Berg Hill Greenleaf Ruscitti, LLP.

(57) ABSTRACT

An electrical stimulation device comprises a stimulation lead with an adjustable length tension sleeve to prevent induction of an electrical current when the electrical stimulation device is in the presence of a magnetic field generated by a device such as an MRI machine. The tension sleeve is shaped to organize excess length of the stimulation lead while providing a variable length between a distal end of the stimulation lead and an electrical source. The shape of the tension sleeve avoids coils and may utilize combinations of straight and curved legs that lie substantially in a common plane to both organize excess length of the stimulation lead and prevent electrical induction.

12 Claims, 14 Drawing Sheets

(56) References Cited

U.S. PATENT DOCUMENTS

| | | | |
|---|---|---|---|
| 7,496,404 B2 | 2/2009 | Meadows et al. |
| 7,672,734 B2 | 3/2010 | Anderson et al. |
| 7,769,462 B2 | 8/2010 | Meadows et al. |
| 7,769,472 B2 | 8/2010 | Gerber |
| 7,822,482 B2 | 10/2010 | Gerber |
| 7,844,343 B2 | 11/2010 | Wahlstrand et al. |
| 7,844,344 B2 | 11/2010 | Whlstrand et al. |
| 7,853,332 B2 | 12/2010 | Olsen et al. |
| 7,877,150 B2 | 1/2011 | Hoegh et al. |
| 7,930,038 B2 | 4/2011 | Zarembo |
| 8,027,736 B2 | 9/2011 | Wahlstrand et al. |
| 8,055,351 B2 | 11/2011 | Atalar et al. |
| 8,335,570 B2 | 12/2012 | McDonald |
| 8,364,279 B2 | 1/2013 | McDonald et al. |
| 8,364,286 B2 | 1/2013 | Hoegh et al. |
| 8,380,324 B2 | 2/2013 | McDonald et al. |
| 8,433,421 B2 | 4/2013 | Atalar et al. |
| 8,442,650 B2 | 5/2013 | Seifert |
| 8,483,844 B2 | 7/2013 | McDonald et al. |
| 8,504,170 B2 | 8/2013 | Wahlstrand et al. |
| 8,571,627 B2 | 10/2013 | Tremblay et al. |
| 8,620,453 B2 | 12/2013 | Wahlstrand et al. |
| 8,620,454 B2 | 12/2013 | Wahlstrand et al. |
| 8,666,511 B2 | 3/2014 | Williams |
| 8,670,839 B2 | 3/2014 | Carbunaru et al. |
| 8,676,340 B2 | 3/2014 | Wahlstrand et al. |
| 8,688,226 B2 | 4/2014 | Atalar et al. |
| 8,694,123 B2 | 4/2014 | Wahlstrand et al. |
| 8,774,939 B2 | 7/2014 | McDonald |
| 8,805,541 B2 | 8/2014 | Wahlstrand et al. |
| 8,818,526 B2 | 8/2014 | McDonald et al. |
| 8,841,908 B2 | 9/2014 | Assmann et al. |
| 8,849,417 B2 | 9/2014 | Olsen et al. |
| 8,868,207 B2 | 10/2014 | McDonald et al. |
| 8,868,208 B2 | 10/2014 | Seifert |
| 8,874,206 B2 | 10/2014 | Malinowski et al. |
| 8,880,187 B2 | 11/2014 | McDonald et al. |
| 2001/0039413 A1* | 11/2001 | Bowe ............ A61M 25/0041 604/532 |
| 2004/0238819 A1 | 12/2004 | Maghribi et al. |
| 2005/0015128 A1 | 1/2005 | Rezai et al. |
| 2005/0222647 A1 | 10/2005 | Wahlstrand et al. |
| 2007/0255367 A1 | 11/2007 | Gerber et al. |
| 2008/0039917 A1 | 2/2008 | Cross et al. |
| 2009/0062883 A1 | 3/2009 | Meadows et al. |
| 2011/0238145 A1 | 9/2011 | Swanson |
| 2011/0257659 A1 | 10/2011 | Mehdizadeh et al. |
| 2013/0106347 A1 | 5/2013 | Kallmyer et al. |
| 2014/0277260 A1 | 9/2014 | Khalil et al. |
| 2014/0277263 A1 | 9/2014 | Khalil et al. |
| 2014/0277264 A1 | 9/2014 | Khalil et al. |
| 2014/0277265 A1 | 9/2014 | Khalil et al. |
| 2014/0277266 A1 | 9/2014 | Khalil et al. |
| 2016/0045724 A1 | 2/2016 | Lee et al. |

* cited by examiner

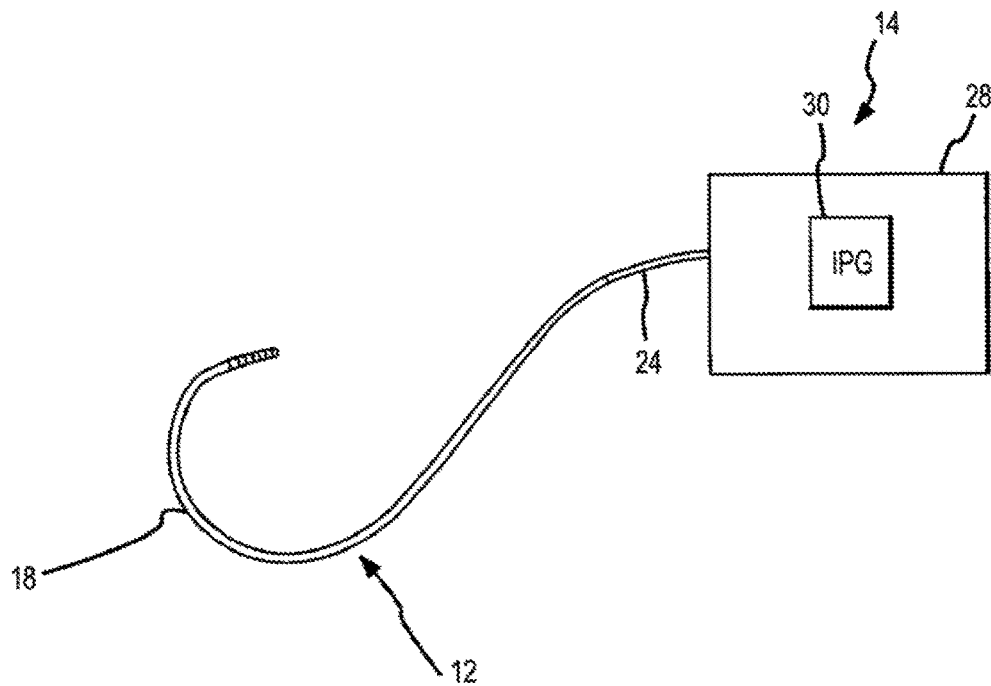
FIG. 5
(Prior Art)
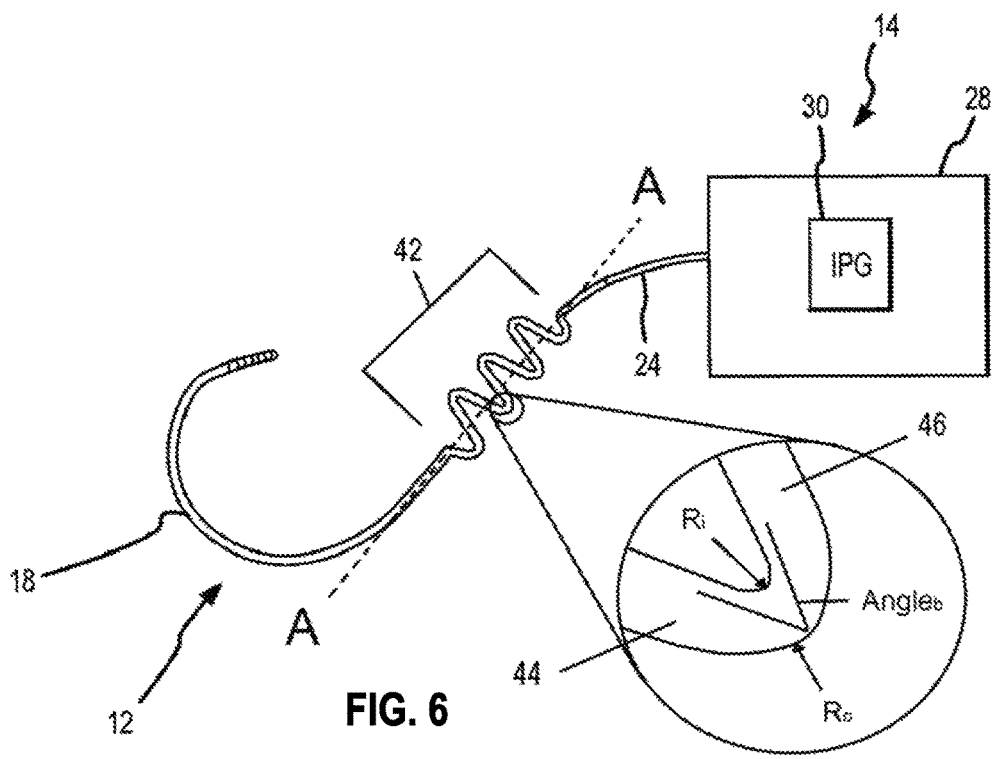
FIG. 6
FIG. 6A

ADJUSTABLE LENGTH TENSION SLEEVE FOR ELECTRICAL OR THERMAL STIMULATION DEVICE

CROSS REFERENCE TO RELATED APPLICATIONS

This application is a continuation-in-part of application Ser. No. 14/639,671 filed on Mar. 5, 2015, the entire disclosure of which is hereby incorporated in its entirety by reference.

FIELD OF THE INVENTION

The invention relates generally to stimulation leads for treatment of medical conditions, and more particularly, to a device and method to organize excess lengths of a stimulation lead without inducing an electrical current from a magnetic field.

BACKGROUND OF THE INVENTION

Spinal cord stimulation (SCS) is a procedure to treat chronic pain wherein a target tissue is stimulated by an electrical lead. SCS is commonly used to treat failed back surgery syndrome and peripheral ischemic pain after more conservative therapies have failed. The lumbar spinal cord is one example of a target tissue which may be subjected to a low intensity electric current from a stimulation lead to treat chronic pain. The amplitude of electric current is on the order of milliamps or volts, and the frequency of the electric current is commonly between 20 and 120 hertz.

While the exact effect of the SCS procedure is not completely understood, it is theorized that the electric stimulation of tissues such as the lumbar spinal cord suppress the excitability of neurons and some amino acids. An electrical stimulator device in its most basic form is a stimulator lead, electrodes disposed on a distal end of the lead, and a source of electrical power interconnected to the stimulation lead. The source of electrical power may be an implantable pulse generator (IPG) or a radio frequency (RF) receiver that receives power from an external transmitter.

A similar type of treatment for chronic pain utilizes radio-frequency energy to induce a thermal lesion in the target tissue. In this type of procedure, the therapeutic benefit is intended to derive from heating the target tissue and not from immersing the tissue in an electrical field. Thus, the electrical lead in this treatment is strictly for use in heating the tissue, and there is no therapeutic electrical field generated.

For both electrical and thermal stimulation, an electrical current generator, commonly referred to as a pulse generator, may be used to transmit a pulse of electrical current to an implanted stimulation lead that has been accurately placed to transmit the electrical or thermal energy from the electrodes to the target tissue in order to treat the particular condition. Implanted pumps and generators can be used to deliver the electrical stimulation as opposed to transdermal delivery devices. More particularly, IPGs are commonly used so that patients do not have to return to a medical facility each time treatment is to be conducted.

The intervertebral disc (IVD) provides separation, shock absorption, and controlled motion between vertebral bodies. The disc is comprised of a central nucleus of a semi-fluid mass of mucoid material, (nucleus pulposus), an outer more dense collagen ring (annulus fibrosis), and a thin, metabolically active cellular layer separating the nucleus and the outer collagen ring, referred to as the annular nuclear interface/transitional zone. Disc nutrition is tenuous at best and is provided by diffusion through the vertebral end plate in contact with the outer surface of the disc. As a result, a disc has limited ability to heal or regenerate. Due to age, injury or other conditions, cracks or fissures may develop in the wall of intervertebral discs causing a chronic source of pain in many patients. Additionally, the inner disc tissue (nucleus) will frequently cause the disc to bulge or herniate into the fissures in the outer region of the disc, thus causing nerve tissue therein to generate pain signals.

Placement of a stimulation lead within a disc can be quite difficult. Because a disc does not have a uniform density, stimulation leads can be quite difficult to place and may require the attending physician to make multiple attempts for proper placement or abandon the procedure. Of course, multiple placement attempts greatly increase the invasive nature of the procedure and therefore create unnecessary tissue damage and increased risk of other ill effects. Inability to perform the procedure denies the patient a therapeutic option. Improper placement of the stimulation lead can also result in the undesirable damage of nerve tissue that is not contributing to the chronic pain or other ailments.

Medical practitioners use magnetic resonance imaging (MRI) machines to help accurately locate the stimulation lead to avoid too many placement attempts. MRI machines commonly use two magnetic fields to orient dipolar molecules for imaging: a pulsed magnetic-gradient field and a pulsed radio-frequency field.

The components of a stimulator can form a loop that induces an electrical current from the MRI's magnetic fields. Excess length of the stimulation lead or conducting wire is often looped to organize the wire such that it does not interfere with other devices or processes. Looped conducting wire also provides a variable length between the distal end of the stimulation lead and the pulsed generator so that a patient can move after a surgery without relocating the lead or generator.

The induction of an electrical current during an MRI procedure can result in severe burns to the patient, who is often under an anesthetic and cannot sense a burning sensation of the electrical current. Examples of prior art devices that address electrical induction in a lead may be found in U.S. Pat. Nos. 8,676,340 and 8,688,226. However, these references do not address electrical induction in a looped stimulation lead or conducting wire. Therefore, there is a need for an electrical stimulation device that can be used in an MRI machine without inducing an electrical current and burning a patient.

SUMMARY OF THE INVENTION

In accordance with the invention, an electrical stimulation device is provided that comprises a stimulation lead with a tension section to prevent induction of an electrical current when the electrical stimulation device is in the presence of a magnetic field generated by devices such as an MRI machine. The tension section is shaped to organize excess length of the stimulation lead while providing a variable length between a distal end of the stimulation lead and an electrical source. The shape of the tension section avoids loops and may utilize combinations of straight and curved legs that lie substantially in a common plane to both organize excess length of the stimulation lead and prevent electrical induction.

The tension section of the stimulation lead may extend between several different lengths depending on the forces applied to the stimulation lead. For example, without any external forces, the tension section may have a first length. When a tensional force is applied to the stimulation lead, the tension section extends to a second length. If the tensional force is removed, the tension section reverts or recoils back to its first length. This aspect of the tension section allows for a variable distance between the distal end of the stimulation lead, which is typically the location of electrodes used to treat tissue, and the proximate end of the stimulation lead, which is typically the location of a lead extension that is operably interconnected to an implantable generator. Thus, when the components of the electrical stimulation device are implanted in a patient and the patient moves his or her body, the tension section accommodates the varying distance between the electrodes placed proximate to a tissue and the generator that is placed elsewhere in the patient's body.

The tension section may be made from a variety of materials. The stimulation lead may be made from a common conductor such as copper, and the tension section made simply be a portion of the lead deformed in a particular shape. In other embodiments, the tension section may be made from a shape-memory alloy. One example of such an alloy is nickel-titanium which has two crystalline phases. In the pre-deformed crystalline phase, the alloy has one shape. Then, in a second crystalline phase, a user may deform the alloy into a second shape. This deformation may be useful when implanting the electrical stimulation device into a patient's body. For example, the stimulation lead may be stretched out and passed through an introducer needle or stylet, which is used to locate the stimulation lead next to a tissue. Once the stimulation lead is positioned and the needle or stylet is removed, heat may be applied to the alloy to revert the alloy back to its first crystalline phase and its pre-deformation shape, which organizes excess stimulation lead length and prevents induction of an electrical current.

While the stimulation lead may be designed to have a tension section to organize excess stimulation lead length while preventing electrical induction, many stimulation leads have already been produced without a tension section. Therefore, it is desirable to retrofit existing stimulation leads with a tension jacket or sleeve to incur the benefits associated with the tension section. The tension sleeve is similar in shape to the tension section, but the tension sleeve comprises a passage or interior volume for an existing stimulation lead to pass through. The tension sleeve shapes at least a portion of the stimulation lead like a tension section. Similarly, a stand-alone tension section may be used to retrofit existing devices. Typically, the stimulation lead has a particular configuration of electrodes that is received in a stimulation source. Thus, a stand-alone tension section has one end configured to receive a proximal end of the stimulation lead and another end configured to insert into a stimulation source. Therefore, a stimulation lead retrofitted with a tension sleeve or a stand-alone tension section can organize excess stimulation lead length and prevent induction of an electrical current when the retrofitted stimulation lead is in the presence of a magnetic field.

According to yet another feature of the invention, a tension sleeve is provided with an adjustable length. The adjustable tension sleeve includes at least one pull tab that is activated to selectively shorten the tension sleeve. Preferably, a pair of pull tabs is provided at one end of the tension sleeve. The pull tabs communicate with at least one line of weakness such as a perforation line, a fold line or some other tension sleeve feature that allows a user to strip away a selected length of the tension sleeve. Once a selected length of the tension sleeve is removed thereby exposing a corresponding length of the stimulation lead or lead extension, the excess tension sleeve can be removed by cutting the excess length. The term "tab" as used herein is intended to cover any type of protrusion or extension that allows a user to grasp the tab and initiate a tear along a selected length of the adjustable tension sleeve. Therefore, this tab is not limited to any particular shape, size, or orientation as it extends from an end of the adjustable tension sleeve.

According to another aspect of the adjustable length tension sleeve, activating pull tabs may be located at both ends of the sleeve so a user can selectively shorten either end of the tension sleeve, or both.

Considering the above described features and attributes, in one aspect of the invention, it can be considered an adjustable length tension sleeve device for an electrical or thermal stimulation device, comprising: a sleeve body having a plurality of legs, the body having a shape that changes lengths between a first relaxed state and a second stressed state, wherein the shape of the body lies substantially in a common plane to prevent induction of an electric current when the stimulation device is subjected to a magnetic field; a first end of the sleeve body terminating adjacent a proximal end of a stimulation lead or a proximal end of a lead extension of the stimulation device; a second end of the sleeve body extending a predetermined length along the stimulation lead and lead extension; at least one tab located at a selected one of the first or second ends of the sleeve body; and a line of weakness extending longitudinally along said sleeve body and communicating with said at least one tab.

In another aspect of the invention, it can be considered an electrical or thermal stimulation device in combination with an adjustable length tension sleeve, comprising: a stimulation lead having a first end, a second end, and at least one conducting wire disposed between the first end and the second end; a plurality of electrodes positioned on the first end of the stimulation lead; a lead extension positioned on the second end of the stimulation lead, the lead extension interconnected with a source of electrical energy, the electrodes communicating with the source of electrical energy for providing electrical or thermal stimulation of tissue proximate to the electrodes; an adjustable length tension sleeve having a shape that changes lengths between a first relaxed state and a second stressed state, wherein the shape of the adjustable tension sleeve lies substantially in a common plane to prevent induction of an electric current when the stimulation device is subjected to a magnetic field, the adjustable length tension sleeve including (a) an internal passage for receiving the stimulation lead and lead extension, (b) at least one tab located at a selected end of the sleeve, and (c) a line of weakness extending longitudinally along said sleeve and communicating with said at least one tab.

In yet another aspect of the invention, it may be considered a method of selectively changing a length of a tension sleeve used with an electrical or thermal stimulation device, the method comprising: providing a stimulation lead having a first end, a second end, and at least one conducting wire disposed between the first end and the second end; providing a plurality of electrodes positioned on the first end of the stimulation lead; providing a lead extension positioned on the second end of the stimulation lead, the electrodes extending through the lead extension and communicating with a source of electrical energy to provide stimulation of tissue proximate to the electrodes; providing an adjustable length tension sleeve mounted over said stimulation lead and lead extension, the adjustable length tension sleeve having a shape that changes between a first relaxed state and a second stressed state, wherein the adjustable length tension sleeve lies substantially in a common plane to prevent induction of an electric current when the stimulation device is subjected to a magnetic field, the adjustable length tension sleeve further having (a) at least one tab located at a selected end of the sleeve, and (b) a line of weakness extending longitudinally along said adjustable length sleeve and communicating with said at least one tab; and activating the at least one tab to strip away a selected length of the adjustable length sleeve to thereby expose a corresponding length of the stimulation lead or lead extension.

According to yet further aspects of the device and method of the invention, the invention may further comprise: (i) wherein said sleeve body further comprises a longitudinal axis extending between said first end and said second end of said body, a first straight leg offset from said axis by a first angle when said shape is in said first relaxed state, and said first straight leg is offset from said axis by a second angle when said shape is in said second stressed state, said first angle is different than said second angle; (ii) wherein said sleeve body further comprises a first curved leg having a first radius when said shape is in said first relaxed state, and said first curved leg having a second radius when said shape is in said second stressed state, said first radius is smaller than said second radius; and (iii) wherein said shape of said sleeve body is not a coil.

Further advantages and features of the invention will become apparent from a review of the following detailed description, taken in conjunction with the drawings.

BRIEF DESCRIPTION OF THE DRAWINGS

Reference is now made to the following detailed description taken in conjunction with the accompanying drawings in order for a more thorough understanding of the invention.

FIG. 5 is a schematic diagram of an electrical stimulation device having a stimulation lead and an implantable pulse generator;

FIG. 6 is a schematic diagram of an electrical stimulation device having a stimulation lead, an implantable pulse generator, and a tension section of the invention;

FIG. 6A is an enlarged view of a portion of the tension section shown in FIG. 6;

DETAILED DESCRIPTION

Figure 1:
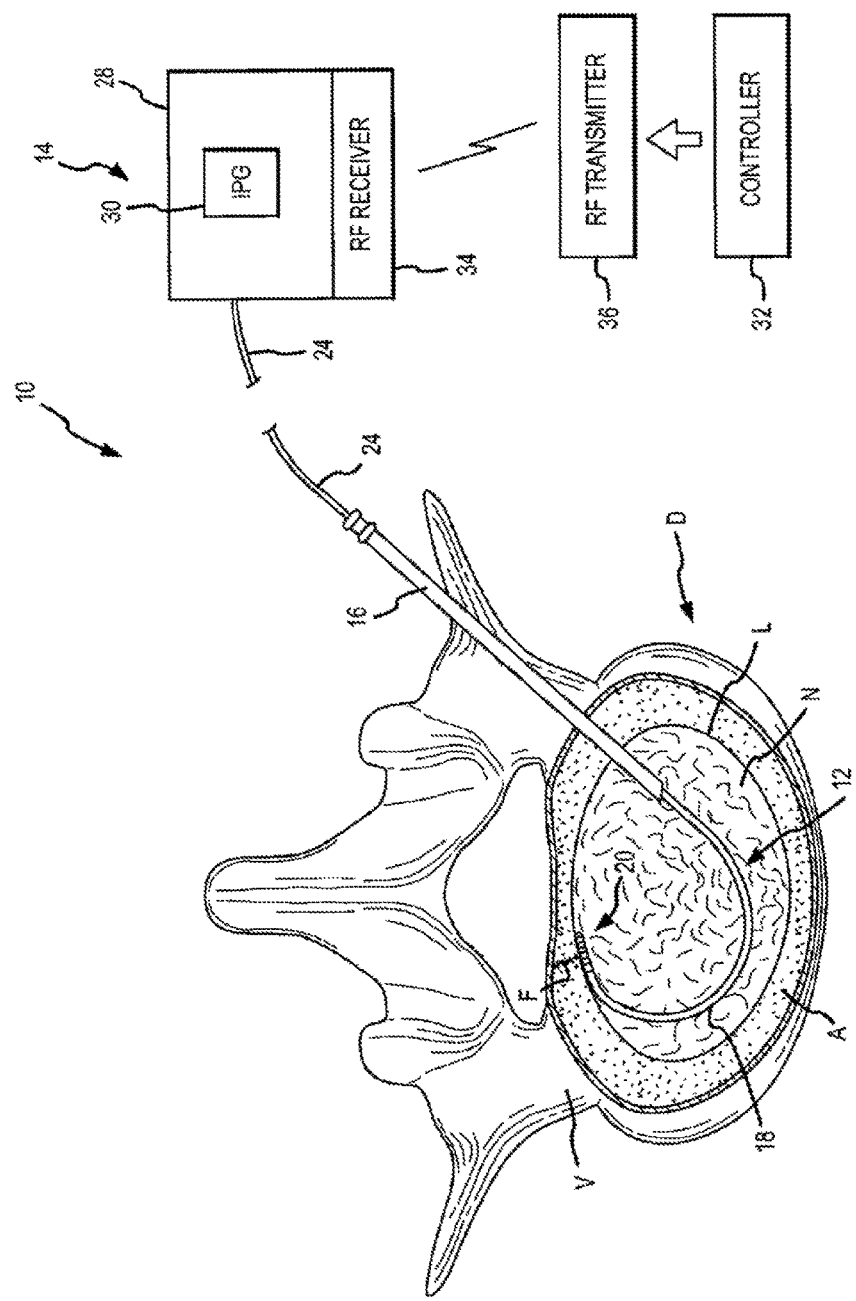
FIG. 1 illustrates a prior art system including a stimulation lead inserted in an intervertebral disc, and an electrical power source that provides a controlled delivery of electrical field energy through the stimulation lead.
Figure 2:
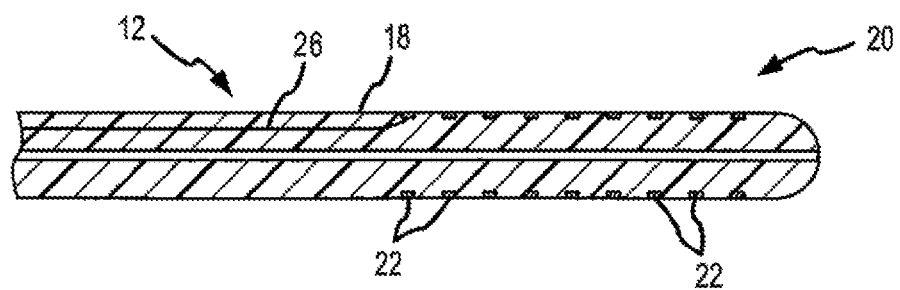
FIG. 2 is an enlarged cross-section of the working distal portion of an example stimulation lead.

Referring to FIGS. 1 and 2, a prior art system 10 is shown that includes an electrical stimulation device 12 and an optional interventional device such as an introducer needle 16 that allows introduction of a stimulation lead 18. If the stimulation lead 18 has sufficient stiffness and strength for the procedure to be conducted, an introducer needle is not required. In other words, a physician may steer the stimulation lead 18 to the desired location without any other device such as an introducer needle. The stimulation device illustrated and described herein is to be considered any known stimulation device that can be used in either electrical or thermal stimulation procedures.

FIG. 1 shows use of the stimulation device 12 for purposes of electrical or thermal stimulation of an intervertebral disc D, it being understood that reference to treatment of the intervertebral disc D is but one example of a procedure that can be conducted with the system. The system 10 further comprises a stimulation source 14 that communicates with the stimulation device 12 for delivering electrical energy to the stimulation device 12. A portion of the stimulation device 12 is shown as inserted within the intervertebral disc D. The electrical stimulation device 12 more particularly includes a percutaneous stimulation lead 18 in the form of an elongate tubular member allowing the lead 18 to be placed within the intervertebral disc of the patient to be treated. The working distal portion 20 of the stimulation lead 18 provides the desired stimulation through a plurality of electrodes 22 which are selectively positioned on the distal portion 20. A lead extension 24 may be disposed on the proximal portion of the stimulation lead 18 to connect to the stimulation lead 18 to the simulation source 14. The lead extension 24 can be made of the same type and diameter material as the stimulation lead 18, or may be made of a different type of material and diameter. The lead extension 24 may simply be the end of conducting wires of the stimulation lead or a series of electrodes that correspond to a particular simulation source 14.

Referring specifically to FIG. 2, one example of construction details for the stimulation device 12 shows a plurality of circumferentially extending electrodes 22 positioned at the distal portion 20 of the stimulation lead 18. The electrodes 22 are also spaced longitudinally along the distal portion 20. The electrodes 22 produce an array of electrical field energy, and the target tissue is immersed in the electrical field. One or more electrical conductors 26 extend through the interior of the stimulation lead 18 in order to transmit the electrical impulses to the electrodes 22.

Referring again to FIG. 1 according to one example method of emplacement of the stimulation device 12, a stylet (not shown) is first inserted through the introducer needle 16. The introducer needle 16 is emplaced by penetrating the skin and muscle tissue, and ultimately into the disc D. When the introducer needle 16 has penetrated the disc, the stylet is removed and the stimulation lead 18 is then inserted through a lumen of the introducer needle 16. The stimulation lead 18 is illustrated as being emplaced within the disc D. This disc D is shown in cross section along with an adjacent vertebra V. The stimulation lead 18 is shown as taking an arcuate or curved path through the disc nucleus N in order to be accurately positioned at the area of the disc to be treated, illustrated as a fissure F which has developed adjacent the spinal fluid sac (not shown). The other primary features of the disk D are also illustrated including the annulus fibrosis A and the thin layer L defining the annular nuclear interface/transitional zone.

The stimulation source 14 may be an implantable medical device 28 including an IPG (implantable pulse generator) 30. The IPG 30 can be a self-contained device with internal control for preset delivery of electrical pulses. Alternatively, an external controller 32 could be used to modify the desired treatment protocol by use of RF transmission wherein an implantable RF receiver 34 is integrated with the IPG 30. The controller 32 provides the specific instruction set for transmission by the RF transmitter 36. The RF receiver 34 could also be housed within the same implantable medical device 28, or could be a separate implanted device. An external RF transmitter 36 transmits RF signals to control the delivery of electrical stimulation to the stimulation lead 18.

Imaging devices may be used to position the stimulation lead 18 and the electrodes 22 relative to a specific area of interest inside of a patient's body. A magnetic resonance imaging (MRI) machine is one such device. MRI machines use magnetic fields, radiofrequencies, and computer software to produce detailed images inside of the patient's body. MRI machines envelope the patient in a magnetic field, and the MRI machine then sends pulsed radio waves from a scanner. The magnetic field aligns hydrogen atoms in the patient's body, and the pulsed radio waves knock the hydrogen atoms out of alignment. The resulting response of the hydrogen atoms returning to alignment is used to generate images of structures inside of the patient's body. MRI among other methods may be used to accurately locate the electrodes 22 and the stimulation lead 18 next to areas that need treatment such as nerve tissue.

Figure 3:
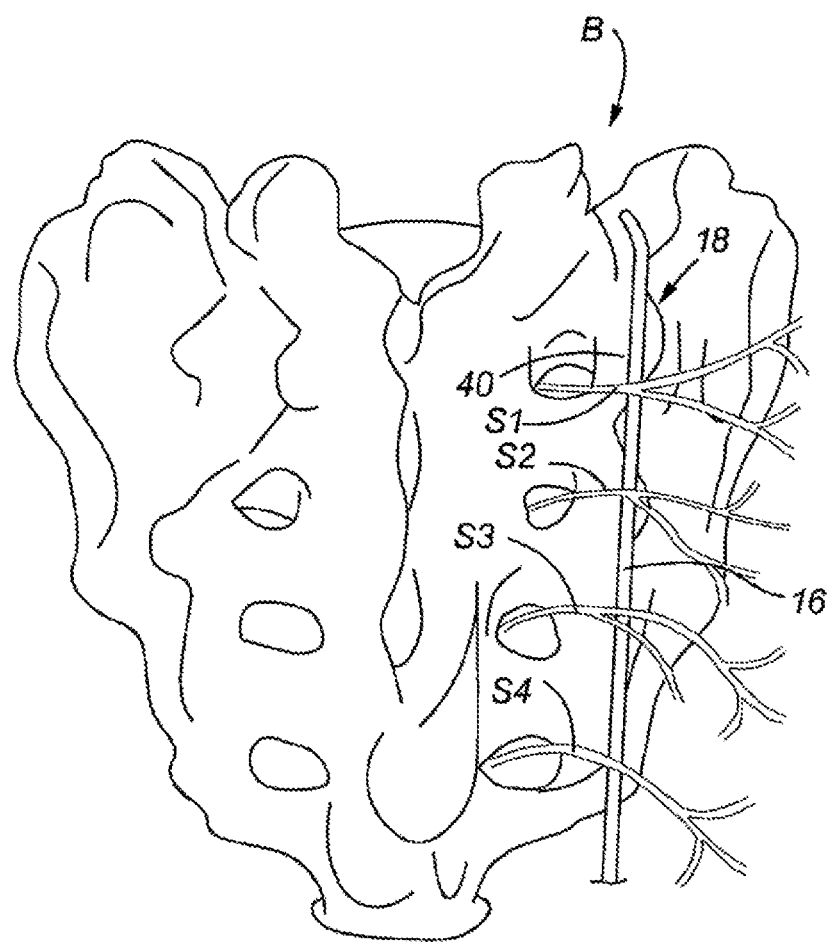
FIG. 3 is a posterior/dorsal view of a sacroiliac region of a patient with an introducer needle inserted along the SI joint.

Referring now to FIG. 3, another example use for a stimulation device may be treatment of SI joint ailments. FIG. 3 specifically illustrates a posterior view of a sacroiliac region with an introducer needle 16 inserted along the sacroiliac region to a targeted area adjacent the SI joint J. According to one method of emplacement of the stimulation device for treatment of the SI joint, the introducer needle 16 is first inserted through the skin below and slightly medial to the inferior aspect to the SI joint and directed towards the inferior lateral edge of the sacrum. The introducer needle 16 is advanced to contact the dorsal aspect of the sacrum at the posterolateral edge. The needle 16 may have a slight curvature near the distal end thereof, shown as curve or bend 40, and the curvature of the bend 40 is then utilized to advance the needle lateral to the sacral foramen and medial to the dorsal aspect of the SI joint. The needle 16 preferably remains in contact with the periosteum along the entire curvature of the sacrum. The needle tip ultimately advances to the superior edge of the sacrum lateral to the sacral foramen and medial to the SI joint. Appropriate positioning of the introducing needle is confirmed preferably both on Antero-posterior (AP) as well as lateral views, such as through MRI imaging.

Figure 4:
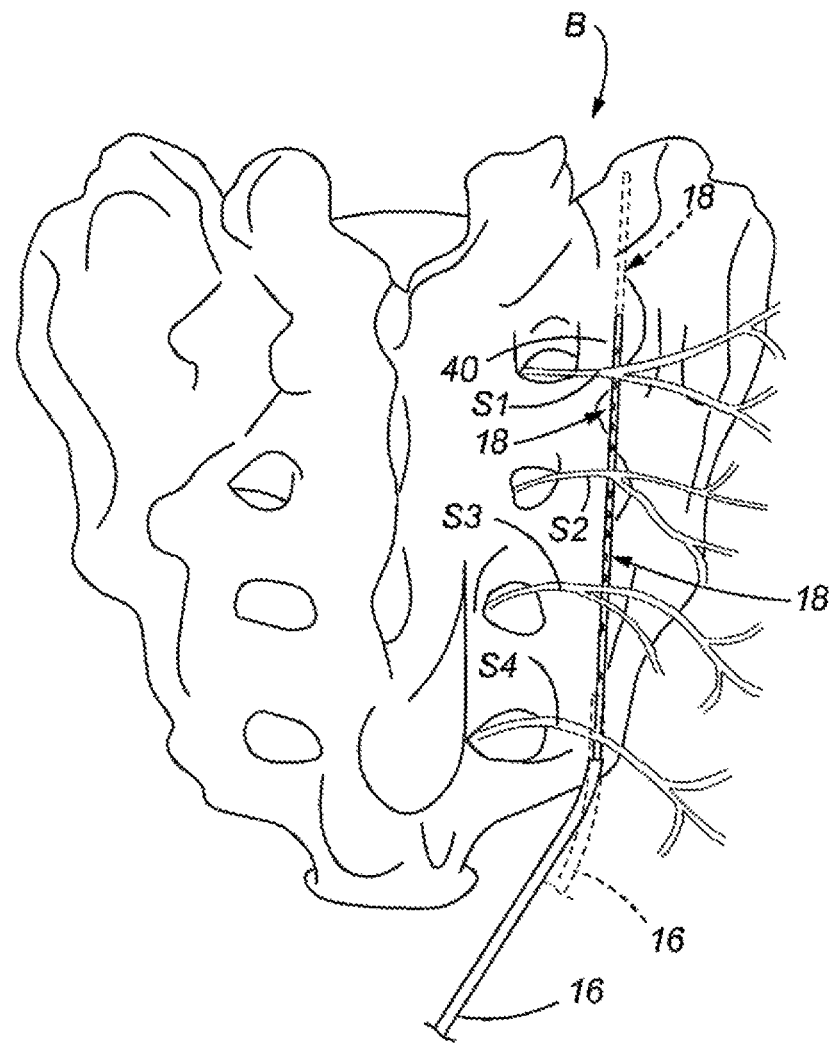
FIG. 4 is an enlarged anterior view of the sacrum bone showing the introducer needle withdrawn a selected length thereby exposing a specific number or group of electrical contacts/electrodes for treatment of selected sacral nerves.

Referring to FIG. 4, the introducer needle 16 is withdrawn along a selected length of the stimulation lead 46 to expose the active number of electrodes 22 necessary to treat the sacral nerve innervation to the SI joint. The dotted lines shown in FIG. 4 for lead 18 represent the initial position of the lead after the needle 16 is withdrawn. The electrodes 22 may then be activated to treat the surrounding neural tissue via denervation (thermal energy) or electric field therapy (electrical energy). The dotted lines for needle 16 in FIG. 4 represent the position of the needle after it has been withdrawn and the lead is ready for activation. The solid lines in FIG. 4 represent the next position of the lead 18 and needle 16 wherein both have been further withdrawn for purposes of conducting another activation to further treat tissue, such as a circumstance when an initial ablation did not effectively cover the desired area of tissue.

Another example use for a stimulation device for treatment of SI joint ailments, but a device that does not require an introducer needle, is the Simplicity™ radiofrequency probe/stimulation device sold by NeuroTherm®. This device is a self-contained disposable probe that allows for a single insertion point to create a continuous strip lesion of sufficient size for effective SI medial nerve branch denervation. The single insertion point eliminates the need for multiple needle placements around each sacral foramen, therefore reducing procedure time and increasing patient comfort.

FIG. 5 illustrates an electrical stimulation device 12 configured to interconnect to a stimulation source 14, which could be an implantable medical device 28 with a pulse generator 30. The portion of the lead 18 running between the electrodes and the lead extension 24 may comprise a conducting wire such that the electrical signal from the source 14 is conveyed to the electrodes.

During a spinal cord stimulator surgery, the entire stimulation device 18 and medical device 28 are implanted inside of the patient's body. The distal end of the stimulation lead 18 is located proximate to an area of interest such as nerve tissue, then the medical device 28 is implanted under the skin in the upper buttock or abdomen regions. This type of surgery is often successful in alleviating chronic pain and allowing the patient to return to an active lifestyle. However, when the patient's body flexes and moves during activities, the distance between the distal end of the lead 18 and the medical device 28 is not constant. In other words, if the stimulation lead 18 had a fixed length, then the distal end of the lead 18 and/or the medical device 28 is in danger of moving out of place when the patient moves during activities.

According to an embodiment of the invention illustrated in FIG. 6, a tension section 42 allows for a variable distance between the lead 18 and the medical device 28 without risking induction of an electrical current from an MRI machine when a physician uses an MRI machine to accurately position the distal end of the lead 18. The tension section 42 as illustrated is capable of changing lengths to accommodate varying distances between the lead 18 and the medical device 28 as a patient moves his or her body. The tension section 42 is generally a section of the lead 18 or conducting wire that has one or more legs offset from a central longitudinal axis A-A oriented along the non-tension section parts of the lead 18. In the embodiment illustrated in FIG. 6, the tension section 42 has multiple portions or legs that are configured like an accordion such that the lead 18 can change to a lengthened state under a tensional force, and change to a shortened state under a compressive force. Collectively, the lengthened state and the shortened state are defined herein by a stressed state, meaning there are external forces applied to the tension section 42. Forces other than tension or compression forces acting along a longitudinal axis may be applied to the tension section 42. For example, torsion may be applied to the tension section 42 that causes a moment force or shearing force. The tension section 42 is still be defined by a lengthened state or a shortened state when torsion is applied because a moment force or a shearing force affects the length of the tension section 42.

Further, each of the legs of the tension section 42 may lie substantially in a common plane when the tension section 42 is in a relaxed state (i.e. no external forces applying a force to the tension section 42) or a stressed state such as a lengthened state or a shortened state so as not to induce an electrical current when the lead 18 is in the presence of a magnetic field.

The tension section 42 is in a relaxed state in FIG. 6, but the electrical stimulation device is not necessarily implanted with the tension section 42 in a relaxed state. It may be advantageous to pre-load or implant the electrical stimulation device with the tension section 42 under a tensional force. Therefore, when the electrical stimulation device is subjected to compressive forces in the body, the tension section 42 naturally compresses toward its relaxed state shape and does not bunch up or buckle out of plane. Similarly, it will be appreciated that it may also be advantageous in some circumstances to pre-load the tension section 42 with a compressive force when the electrical stimulation device is implanted in the body.

The legs of the tension section 42 may not lie substantially in a single flat, linear plane once the devices 18, 28 are implanted in the body due to a pre-loaded configuration or movement of the patient's body that bends or twists the tension section 42. For example, during use by a patient, multiple planes may define the shape of the tension section 42 when the tension section 42 is in a relaxed state, lengthened state, or shortened state. Accordingly, the shape of a first and second leg may be defined by a first plane, and the shape of a third and fourth leg may be defined by a second plane. However, regardless of any multi-planar configurations of the tension section that may be found during patient use, the linear or straight legs in combination prevent the tension section 42 from being shaped into a coil.

FIG. 6A shows an enlarged portion of the tension section 42, specifically a bend between a first leg 44 and a second leg 46. The bend in this embodiment is rounded to accommodate a turn or change in the direction of the tension section 42 whereas a sharp turn may result in an over-stressed crimp or fold that would damage the interior conducting wire(s). The geometry of the bend may be described in terms of a bend angle $angle_b$, an inner radius $R_i$, and an outer radius $R_o$. $Angle_b$ is the angle between the longitudinal axes of the first leg 44 and the second leg 46. If a tensional force is applied to the tension section 12, then $angle_b$ increases. After a tensional force has been removed and the tension section 12 reverts back to its relaxed state, then $angle_b$ decreases. In some embodiments $angle_b$ is between approximately 5° and 75°, wherein "approximately" implies variation of +/−10%. In various embodiments, the $angle_b$ is between approximately 30° and 45°.

The joint between the first and second legs 44, 46 may be radiused or chamfered by a desired amount to create a tension section 42 that has a sufficient compact size yet does not compromise an allowable bend angle of the interior conducting wires, which is the smallest or largest $angle_b$ before the conducting wires experience structural damage. The inner radius $R_i$ and the outer radius $R_o$ can define a bend between two legs with a radiused inner portion and a radiused outer portion. In some embodiments the inner radius Ri is between approximately 0.05" and 1". In various embodiments, the inner radius Ri is between approximately 0.15" and 0.35". In some embodiments the outer radius Ro is between approximately 0.05" and 1". In various embodiments, the outer radius Ro is between approximately 0.15" and 0.35".

Figure 7:
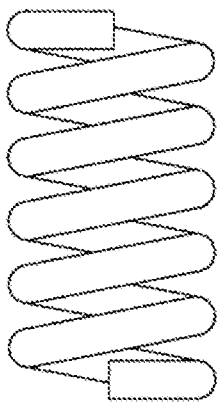
FIG. 7 is a side view of a prior art tension device.

Now referring to FIG. 7, a side view of a prior art tension device is shown. The prior art tension device has a coil shape to organize and shorten excess length of stimulation lead conductors. The coil shape can extend under a tensional force and then retract to its original shape. One problem with this type of tension device is that some three dimensional shapes, such as a coil, will induce an electrical current in the presence of a magnetic field (e.g., an MRI machine) and can therefore potentially burn a patient. The geometry of the helical coil depicted in FIG. 7 can be described in terms of the number of turns, the diameter of the turns, and the thickness of the materials used to make the coil. However, the simple helical coil depicted in FIG. 7 is not the only shape that can induce an electrical current in the presence of a magnetic field. For example, a coil with one turn, or slightly less than one complete turn, can induce an electrical current. Therefore, it will be appreciated that the term "coil" also encompasses a wound spiral shape that turns upon itself or otherwise induces an electric current in the presence of magnetic field. As such, the shape of the stimulation lead and/or the tension section is not a coil.

Figure 8:
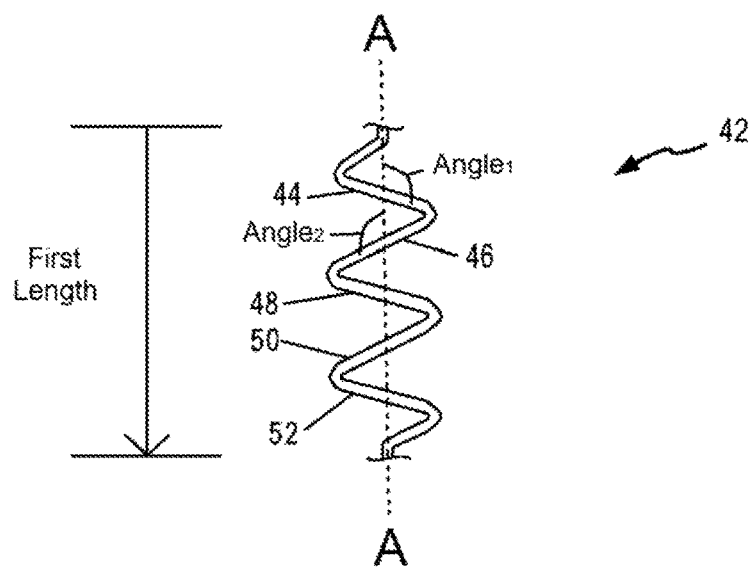
FIGS. 8-10 depict a tension section of the invention and a stimulation lead wherein the tension section extends between three positions.
Figure 9:
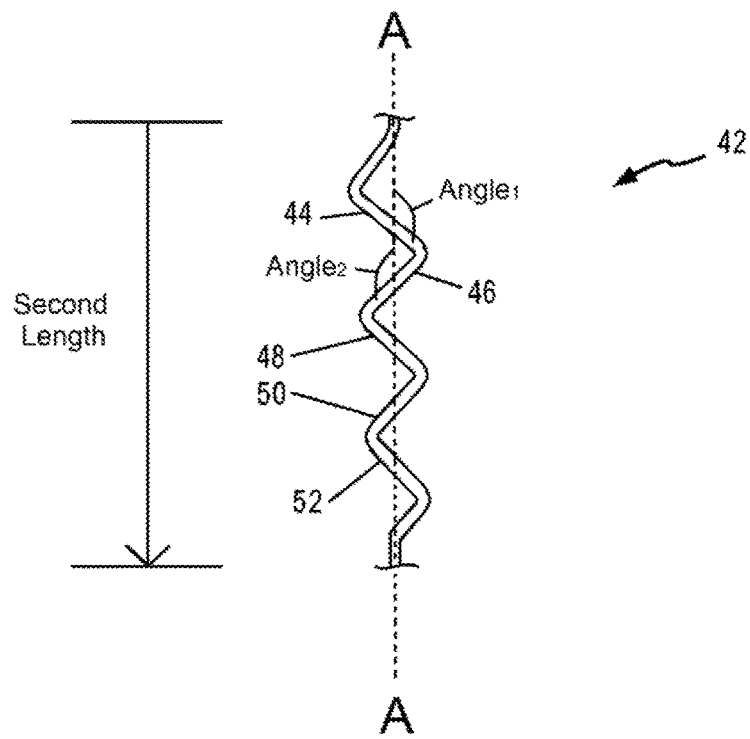
Figure 10:
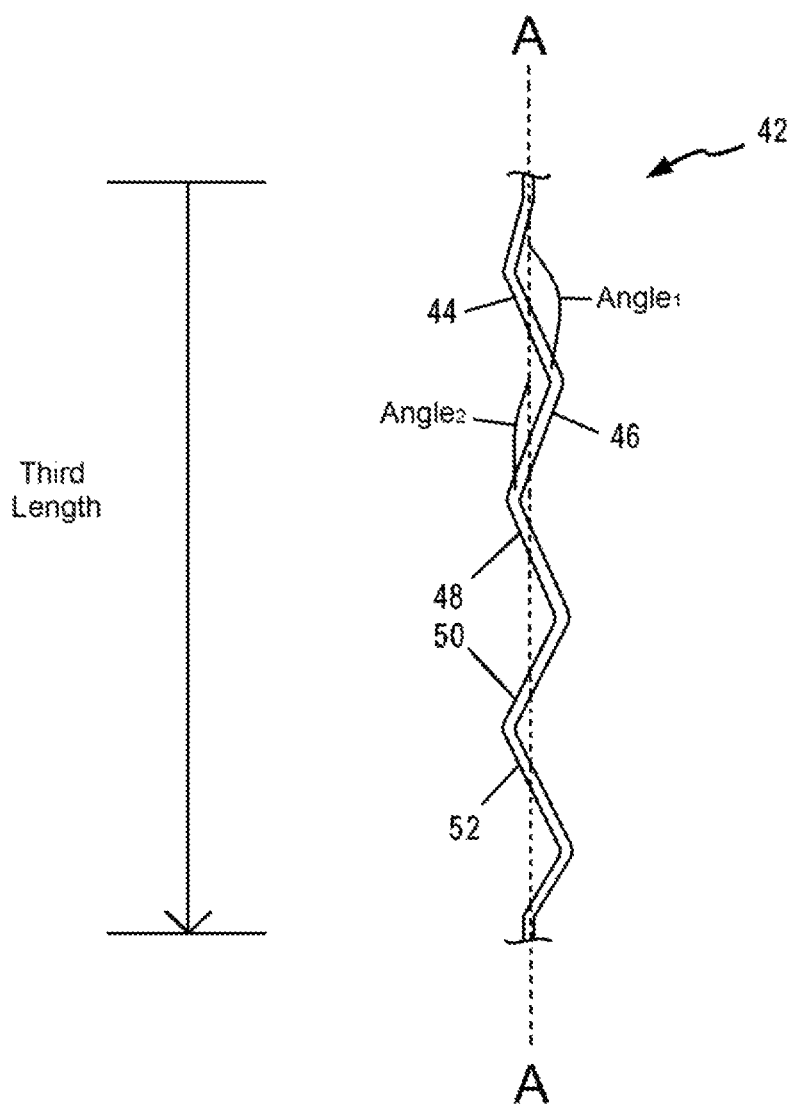

Now referring to FIGS. 8-10, the tension section 42 of the invention may change between multiple lengths. FIG. 8 illustrates a tension section 42 having a first leg 44, a second leg 46, a third leg 48, a fourth leg 50, and a fifth leg 52. These legs 44, 46, 48, 50, 52 are generally straight or linear, and the legs 44, 46, 48, 50, 52 are configured such that the tension section 42 is shaped like an accordion. The legs 44, 46, 48, 50, 52 form angles with a central longitudinal axis A-A, wherein the axis A-A represents the longitudinal axis of the overall stimulation lead 18. The first leg 44 forms an $angle_1$ with the axis A-A, and the second leg 46 forms an $angle_2$ with the axis A-A. In the embodiment shown in FIG. 8, the angles between the legs 44, 46, 48, 50, 52 and the axis A-A are substantially equal to one another. It will be appreciated that in other embodiments, the angles may not be the same. For example, the angles could become progressively larger at a selected end, and in other embodiments, the angles could become progressively smaller. In yet other embodiments, the angles follow no recognizable progression and may be disjointed or random in sequence. In addition, the legs 44, 46, 48, 50, 52 are generally symmetric about the axis A-A, meaning each leg 44, 46, 48, 50, 52 has an equal portion on either side of the axis A-A. In some embodiments, the legs 44, 46, 48, 50, 52 are not symmetric about the axis A-A and may be completely positioned on one side of the axis A-A. In some embodiments the angle between the legs 44, 46, 48, 50, 52 and the axis A-A is between approximately 15° and 75°. In various embodiments, the angle between the legs 44, 46, 48, 50, 52 and the axis A-A is between approximately 30° and 45°.

Further, it will be appreciated that embodiments of the invention may not be limited to five legs 44, 46, 48, 50, 52. The simplest tension section 42 may have two legs. In other embodiments, the tension section 42 may have three legs, four legs, six legs, etc. The number of legs could be modified based on the anticipated extended and retracted length required for the particular use of the tension section 42. The shape of the legs is also not limited to an accordion shape. Other tension section 42 shapes are described elsewhere herein but may also include, without limitation, a sinusoidal shape, a square waveform shape, and a sawtooth waveform shape. The length of a straight leg in various embodiments is between approximately 0.1" and 10". In some embodiments, the length of each of the straight legs may be between approximately 1" and 2". The tension section 42 in FIG. 8 is in a relaxed state with no external forces being applied to the tension section 42. The overall length of the tension section 42 in this relaxed state is a first length.

FIG. 9 illustrates the tension section 42 of FIG. 8 wherein an external force is applying tension along the longitudinal length of the stimulation lead. The real-world source of this tensional force may be a person bending over at the waist such that the distance between the distal end of the lead and the medical device increases, thus subjecting the lead to a tensional force. The accordion shape of the legs 44, 46, 48, 50, 52 begins to stretch out as the tensional force is applied. The angles between each of the legs 44, 46, 48, 50, 52 and axis A-A become more obtuse or larger. The overall length of the tension section 42 in FIG. 9 is a second length. Due to the tensional force, the second length is longer than the first length in FIG. 8.

FIG. 10 depicts a tension section 42 that is subjected to a tensional force greater than the tensional force depicted in FIG. 9. Here, the accordion shape of the tension section 42 is almost gone, and the legs 44, 46, 48, 50, 52 are nearly straightened. Put another way, the angles between the legs 44, 46, 48, 50, 52 an axis A-A are nearly 180°. The overall length of the tension section 42 in FIG. 10 is a third length. Since the tension section 42 is nearly straightened in FIG. 10, the third length is longer than both the first length and the second length.

The stimulation lead 18 and the tension section 42 of the lead 18 may be comprised of a variety of materials. The stimulation lead 18 may be made from a homogeneous material, or may be made from several materials that cause the stimulation lead to have either a more progressively stiff or more progressively flexible characteristics as the lead changes length. Depending upon the manner in which the stimulation lead is to be emplaced, it may be desirable to use either the more progressively stiff or more progressively flexible arrangement. The stimulation lead 18 and the tension section 42 may be made of a traditional material or materials that are conductive such as resins or metals such as copper. In other embodiments, the lead 18 and/or the tension section 42 may be made of a shape-memory alloy. This type of alloy is deformable but reverts back to its pre-deformed shape when heat is applied to the alloy. The heating transforms the crystalline structure of the materials such that the material reverts back to its pre-deformed shape. Therefore, the tension section 42 may have a pre-deformed shape as described herein, then a user may deform the tension section 42 while placing the stimulation lead 18 and the medical device 48, then heat the tension section 42 to revert the tension section 42 to its pre-deformed shape.

Examples of shape-memory alloys include copper-aluminum-nickel (approximately 14-14.5% Al and approximately 3-4.5% Ni), nickel-titanium (approximately 55% Ni), iron-manganese-silicon, copper-zinc-aluminum, copper-zinc-aluminum, copper-zinc-tin, silver-cadmium (approximately 44-49% cadmium), gold-cadmium (approximately 46.5-50% cadmium), copper-tin (approximately 15% tin), copper-zinc (approximately 38.5-41.5% zinc), iron-platinum (approximately 25% platinum), manganese copper (approximately 5-35% copper), various platinum alloys, cobalt-nickel-aluminum, cobalt-nickel-gallium, nickel-iron-gallium, titanium-palladium, nickel-titanium-niobium, nickel-manganese-gallium, and copper-aluminum-nickel.

Figure 11:
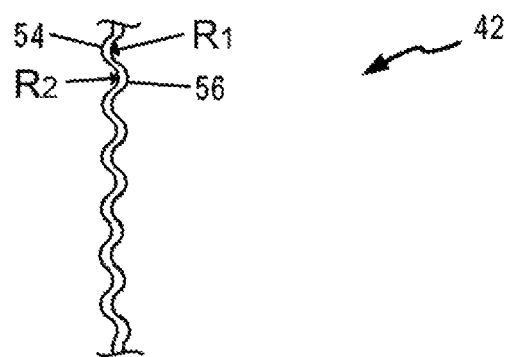
FIG. 11 is a side view of a stimulation lead having a tension section with curved legs.

Now referring to FIG. 11, the tension section 42 may have legs that are curved rather than the straight legs 44, 46, 48, 50, 52 depicted in FIGS. 8-10. The tension section 42 in FIG. 11 comprises a first curved leg 54, a second curved leg 56, and several other curved legs. The first curved leg 54 has a first radius $R_1$, and the second curved leg 56 has a second radius $R_2$ wherein the first radius $R_1$ is equal to the second radius $R_2$. It will be appreciated that embodiments may have a first radius $R_1$ that is larger or smaller than a second radius $R_2$. Further, it will be appreciated that in various embodiments the radii of the legs may become progressively larger, and in other embodiments, the radii may become progressively smaller. In yet other embodiments, the radii follow no recognizable progression and may be disjointed or random in sequence. In addition, the curved legs are generally symmetric about the axis A-A, meaning each leg has an equal portion on either side of the axis A-A. In some embodiments, the legs are not symmetric about the axis A-A and may be completely positioned on one side of the axis A-A. The radius of a curved leg, in some embodiments, is between approximately 0.1" and 10". In various embodiments, the radius of the curved leg is between approximately 0.5" and 1". In further embodiments, the curved legs 50, 52 may not have constant radius. Rather, the curved legs 54, 56 may be adapted to fit a spline defined by an n-order polynomial where n=1, 2, 3, 4, etc.

Figure 12:
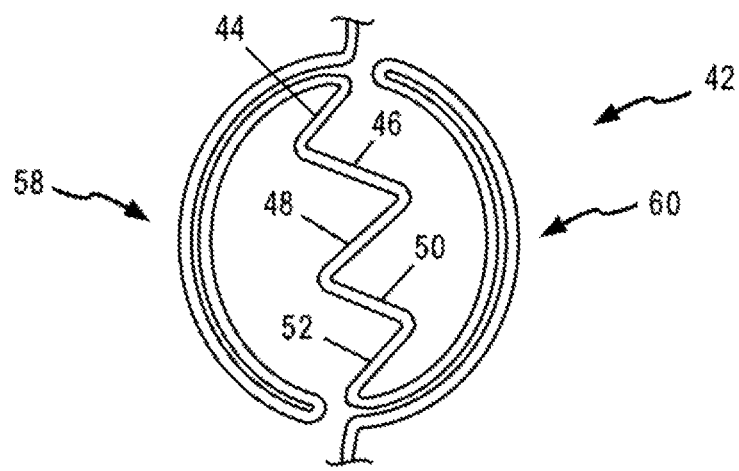
FIG. 12 is a side view of a stimulation lead having a tension section with both straight legs and switchback legs.

FIG. 12 shows an embodiment of the tension section 42 that utilizes both straight and curved legs. Five straight legs 44, 46, 48, 50, 52 are arranged in an accordion-like shape. A first switchback leg 58 is interconnected to the first straight leg 44, and a second switchback leg 60 is interconnected to the fifth straight leg 52. Together, the first and second switchback legs 58, 60 form a shape with a constant diameter. However, as with the curved legs in FIG. 11, the first and second switchback legs 58, 60 are not limited to embodiments with a constant diameter. In other embodiments, the switchback legs 58, 60 may be a shape defined by a spline. In addition, while the straight 44, 46, 48, 50, 52 and switchback 58, 60 legs lie in a common plane in FIG. 12, in other embodiments, the straight legs 44, 46, 48, 50, 52 and the switchback legs 58, 60 do not lie in a single plane as this configuration does not present a risk of inducing an electrical current in the presence of a magnetic field since there is no characteristic coil or helical coil shape.

Figure 13:
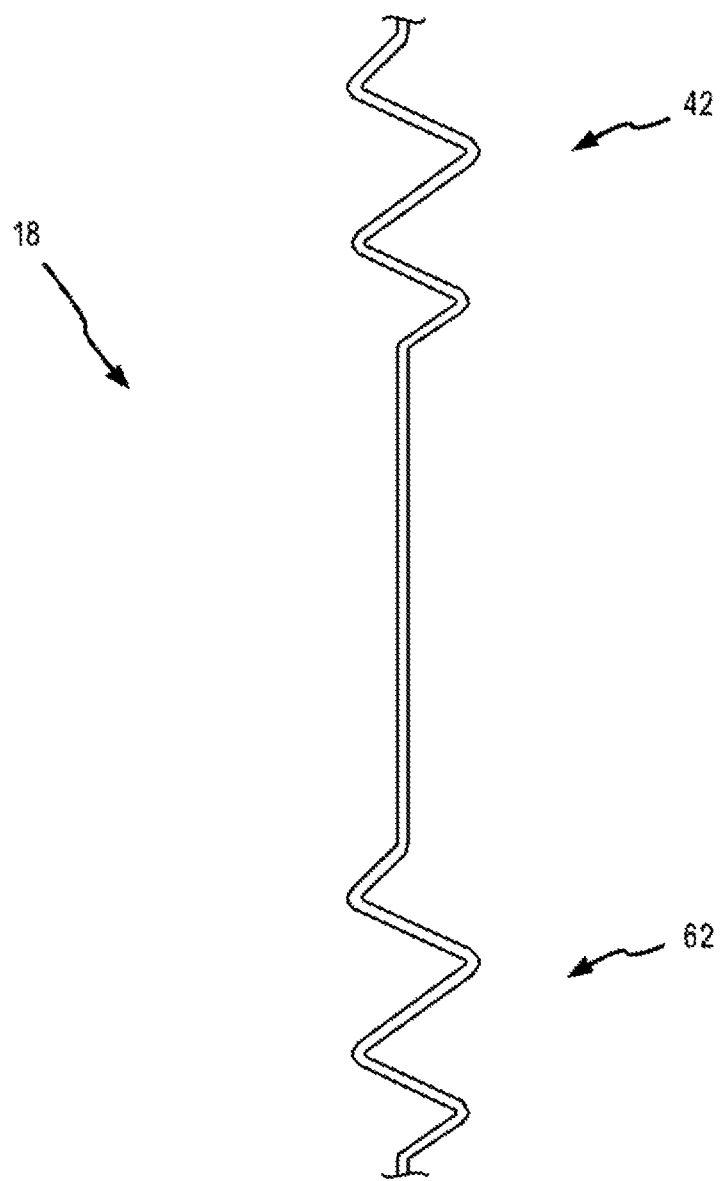
FIG. 13 is a side view of an electrical stimulation device having a first tension section and a second tension section.

Now referring to FIG. 13, a stimulation lead 18 with a first tension section 42 and a second tension section 62 is provided. Embodiments of the invention are not limited to single-tension section configurations. Any number of tension sections may be disposed on the stimulation lead 18. In one embodiment, a first tension section 42 may be disposed proximate to the lead extension and a second tension section 62 may be disposed proximate to the electrodes on the distal end of the stimulation lead 18.

Figure 14:
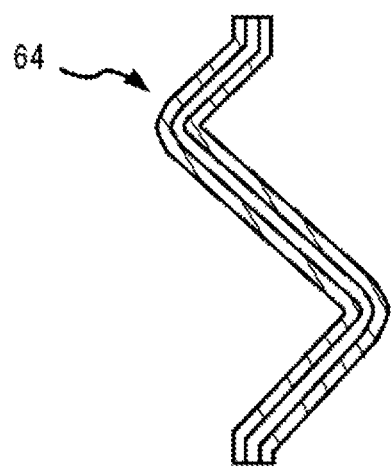
FIG. 14 is a cross-sectional view of a tension sleeve of the invention.

Now referring to FIG. 14, a cross-sectional view of a tension jacket or sleeve 64 is provided. Stimulation leads 18 may be designed and produced with a tension section 42. However, there are numerous stimulation leads 18 used for spinal cord stimulation, nerve denervation, and other procedures that may require the use of a magnetic field that have already been produced without a tension section. The tension sleeve 64 can retrofit existing stimulation leads to achieve the benefits of stimulation leads that have been designed to include a tension section. The tension sleeve 64 may have a less aggressive curvature for each leg due to residual stiffness in the existing stimulation lead.

The cross-sectional view of the tension sleeve 64 in FIG. 14 shows that the tension sleeve 64 has a passage or interior volume running from a first end to a second end. A user may thread an existing stimulation lead into one end, through the tension sleeve 64, and out of the other end.

There are several ways to accomplish this retrofit of an existing stimulation lead. The stimulation lead may be flexible and pliable enough to negotiate any turns in the tension sleeve 64 if the tension sleeve 64 is rigid. A medical lubricant may be used to reduce the friction between the stimulation lead and the tension sleeve 64. In other embodiments, the tension sleeve 64 itself may be flexible and pliable such that a user may pull the tension sleeve 64 straight, then the user may easily thread the stimulation lead through the tension sleeve 64. Once the stimulation lead is through the tension sleeve 64, the user may release the tensional force on the tension sleeve 64, and the tension sleeve 64 will revert back to its original shape. Thus, the stimulation lead will have a shape that organizes excess material from the stimulation lead or conducting wire, and the stimulation lead will be resistant against induction of an electrical current when the stimulation lead is in the presence of a magnetic field. Different embodiments of the tension sleeve 64 may be comprised of a material or materials that optimize between flexibility and elasticity, wherein the flexibility contributes to the tension sleeve's 64 ability to change lengths, and the elasticity contributes to the tension sleeve's 64 ability to revert or recoil to its original or natural shape in a relaxed state.

It should be appreciated that the tension sleeve 64 may be configured like any tension section 42 described elsewhere herein. This includes, but is not limited to, the shapes of the legs, the combination of leg shapes, multiple tension sleeves, etc. There are also a number of ways to manufacture the tension sleeve 64. For example, the tension sleeve 64 may be manufactured to be much longer than necessary including many legs. This gives the user, in most cases a physician, the option to cut the tension sleeve 64 to a specific length. In various embodiments, the stimulation lead has specialized ends, one with electrodes and one with a lead extension configured to interconnect to a medical device. Therefore, the stimulation lead's length is not easily altered, i.e., the stimulation lead cannot be cut to length. However, with different sized patients or different tissues to be targeted, the excess length of stimulation lead that needs to be organized is variable. Therefore, during a procedure, a user may cut to length a specific section of tension sleeve 64 to accommodate the specific requirements of the procedure. In other embodiments, the tension sleeve 64 may come in a variety of sizes and shapes that are not intended to be cut to length, and a user may select a tension sleeve 64 with particular characteristics to suit a specific procedure or patient.

Figure 15:
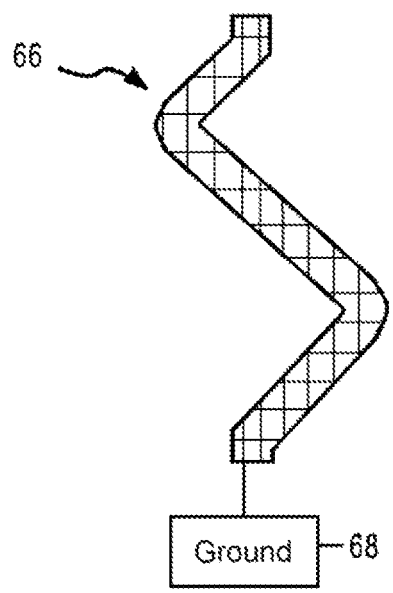
FIG. 15 is a side view of a stimulation lead having an outer surface covered by a mesh that protects the stimulation lead against electromagnetic radiation.

Now referring to FIG. 15, a conductive mesh 66 that surrounds an outer surface of a tension section or a tension sleeve is provided. The mesh 66 provides further protection against induction of electrical current in the presence of a magnetic field by acting as a Faraday cage. The mesh 66 is made from a conductive material such that when the mesh is subjected to electromagnetic radiation, the mesh 66 channels electricity through the mesh 66 and there is constant voltage on all sides of the mesh 66. If the mesh 66 is connected to a ground 68, the mesh 66 may dissipate any electrical currents generated by electromagnetic fields. The mesh 66 may completely envelope the stimulation lead and connect to the medical device. The medical device may have capacitors that store excessive electrical current channeled by the mesh 66 or in other embodiments, the patient's body may serve as a ground 68, and the medical device may safely dissipate the electrical current without concentrating the electrical current and burning the patient.

Figure 16:
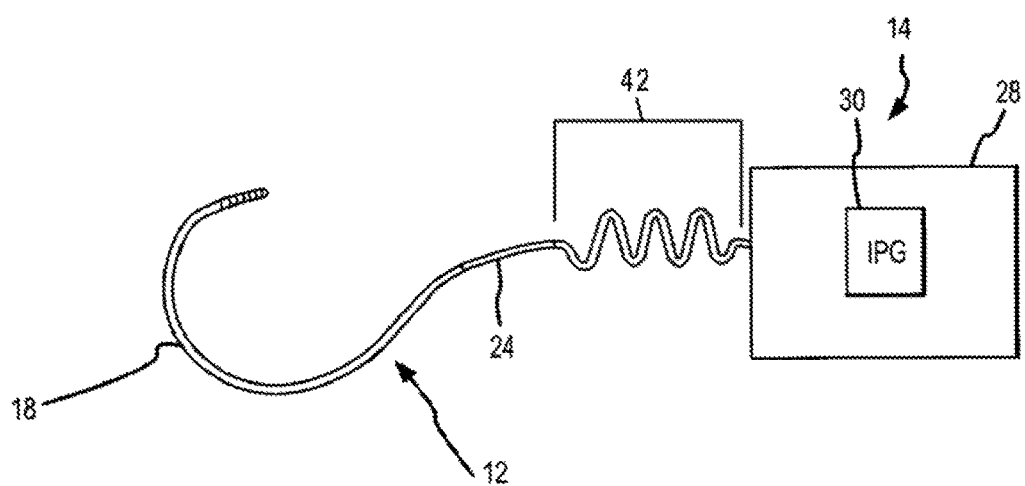
FIG. 16 is a side view of an electrical stimulation device where a tension section is positioned between a lead extension and an implantable generator.

Now referring to FIG. 16, an embodiment of the electrical stimulation device 12 is provided where a tension section 42 is positioned between a lead extension 24 and an a stimulation source 14. As described elsewhere herein, the lead extension 24 is insertable into a stimulation source 14. The lead extension 24 may comprise a series of electrodes that correspond to a particular simulation source 14, which in this embodiment is an implantable medical device 28 with an IPG 30. Therefore, another possible way to retrofit existing stimulation devices is to have a stand-alone tension section 42 that is adapted to receive the electrode configuration of the lead extension 24 and insert a similar or identical electrode configuration into the stimulation device 14. As such, in some embodiments, at least a portion of the tension section 42 is a conducting wire. At one end, the tension section 42 comprises a recess or socket to receive at least a portion of the lead extension 24. At the other end, the tension section 42 is adapted to insert into a recess or socket of the stimulation source 14, just as the lead extension 24 would in other embodiments. It should be appreciated that the tension section 42 may be configured like any tension section 42 described elsewhere herein. This includes, but is not limited to, the shapes of the legs, the combination of leg shapes, multiple tension sleeves, etc.

Figure 17:
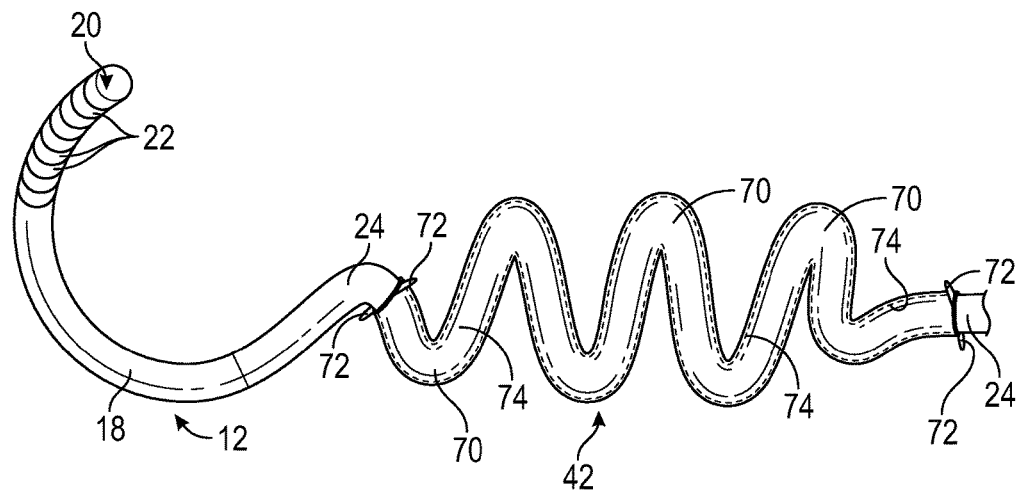
FIG. 17 is a side view of an electrical stimulation device similar to the one illustrated in FIG. 16 and further including an adjustable length tension sleeve.

Referring to FIGS. 17-20, in another embodiment is illustrated for a tension sleeve. This embodiment further adds the capability to adjust a length of the tension sleeve by the user. Referring first to FIG. 17, a tension sleeve or section 42 covers a lead extension 24 over a selected length thereof. A distal end of the tension section 42 has a pair of pull tabs 72. A proximal end of the tension section is also shown with a pair of pull tabs 72. As discussed in more detail with respect to FIG. 20, the tension sleeve/section can be stripped away at either end thereby providing an adjustable length for the tension sleeve.

Figure 18:
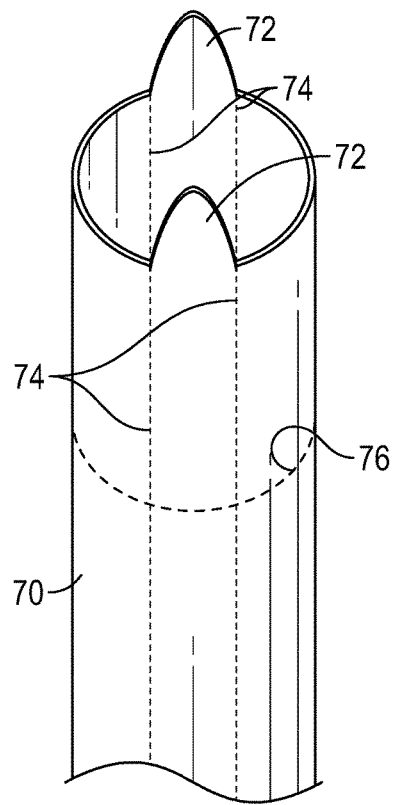
FIG. 18 is an enlarged fragmentary perspective view of an adjustable length tension sleeve illustrating pull tabs oriented in a first longitudinal configuration.

Referring to FIG. 18, the tension sleeve is shown without the lead extension 24 and attached stimulation lead 18 in order to better view structural details of the tension sleeve. As with the prior embodiments, the tension sleeve is a substantially cylindrical element with a hollow interior or chamber that receives a stimulation lead and/or a stimulation lead extension of an electrical stimulation device. In this figure, one end of the tension sleeve is illustrated, which could be either the proximal or distal end of the tension sleeve. A pair of tabs 72 protrudes beyond a distal edge of the body 70 of the tension sleeve as shown. Although a pair of tabs is shown, it should be understood that this embodiment may comprise a single tab, or this embodiment may comprise more than a pair of tabs. The size and shape of the tab 72 can be configured such that the tab is capable of being grasped by a user; therefore, the specific shape of the tabs as illustrated can be modified in other shapes and sizes in order to optimize the ability of the user to grasp the tabs. For example, while the tabs 72 are illustrated as having a symmetrical pointed end, other shapes could include, without limitation, rectangular shapes, oval shapes, triangular shapes, and others. The tabs are preferably nonintrusive in terms of their size and shape such that the tension sleeve may be extended and retracted without interference from the tabs 72.

As also shown in FIG. 18, each edge or side of the tabs communicate with a corresponding line of weakness 74 which allows the tab to be stripped or torn from the remaining portion of the body 70 when a user applies a force to pull the tabs away from the body 70. As mentioned, the lines of weakness may include perforations, fold lines, or other types of weakened areas along the lines 74 which facilitate tearing of the body 70.

Figure 19:
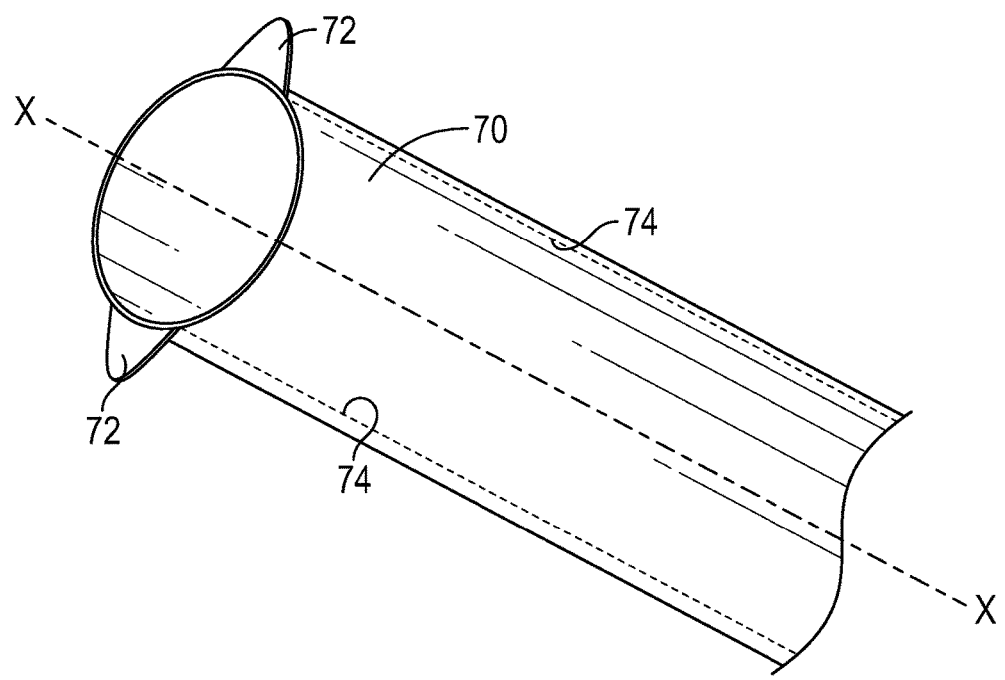
FIG. 19 is an enlarged fragmentary perspective view of the adjustable length tension sleeve illustrating pull tabs oriented in a second transverse configuration.

Referring to FIG. 19, the tabs 72 in this figure are shown as extending substantially perpendicular to the length of the tension sleeve or longitudinal axis X-X of the tension sleeve. In some cases, it may be preferable to have the tabs extend at some angle away from the tension sleeve making it easier for a user to grasp. Therefore, it should also be understood that the particular angular orientation of the tabs can be modified as desired.

The tabs 72 in FIG. 18 are shown as being made of the same material as the body 70. Therefore, the tabs in this figure can be viewed as extensions of the body 70. The tabs in FIG. 19 however are shown as being made from a different material that is attached to the end of the tension sleeve and extending at a different angle away from the tension sleeve. Depending upon the thickness of the tension sleeve material as well as the type of material and ability for the material to incorporate a line of weakness, the tabs 72 may be extensions of the body 70 or may be made from a different material. One objective in choosing the type of tab to incorporate is to select a tab design that allows a user to easily engage a tab and pull the tab to tear the material of the tension sleeve without undue force.

Figure 20:
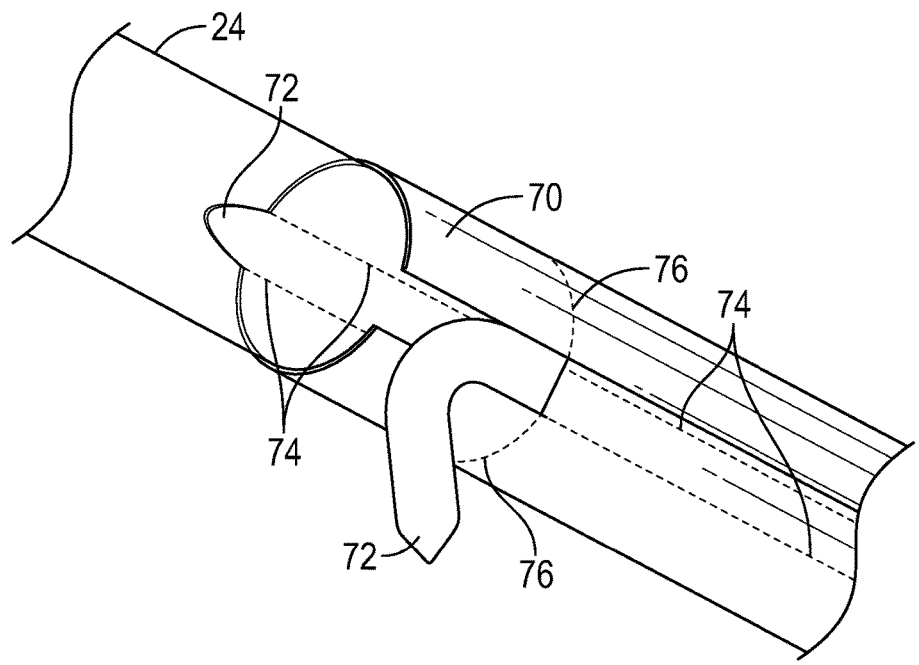
FIG. 20 is an enlarged fragmentary perspective view of the adjustable length tension sleeve illustrating one of the pull tabs activated in order to selectively shorten the length of the tension sleeve thereby lengthening the lead extension.

Referring to FIG. 20, this figure shows one of the tabs activated such that tears are made along the respective lines of weakness 74. A user has the option of activating the other tab 74 to create tears on the other lines of weakness if necessary. Once a sufficient length of the sleeve body has been stripped away, the user may remove the excess material by cutting the material around circumference line 76. The circumference line 76 intersects the location where the tears terminate.

According to the embodiment shown in FIGS. 17-20, tabs placed at either or both ends of the tension sleeve allow user to selectively adjust a length of the tension sleeve. In some circumstances, it may be required to increase a length of portion of the lead extension 24 adjacent the stimulation lead 18 and thus remove the tension sleeve at that location. In other circumstances, the tension sleeve length may need to be reduced at the opposite end towards the stimulation source 14 so that an increased length of the lead extension is exposed. In either circumstance, the adjustable length tension sleeve achieves selective shortening of the tension sleeve at either end thereof.

For each of the embodiments, it is also contemplated that the devices may be constructed of materials that are compatible with the imaging technique used to visualize the procedure being conducted. For X-ray and CT scanning techniques, standard materials are typically imaged in an acceptable fashion. However, if it is desired to use MRI, special consideration may be required in selection of materials so that the device does not create a large image artifact. Two examples of acceptable materials that may be used as MRI compatible include non-magnetic alloys of stainless steel and titanium.

For each embodiment discussed above, it should also be understood that each of the active electrical conductive areas or electrodes may be independently connected to a source of power such that each of the electrodes may be selectively energized or de-energized to provide the desired ablative pattern or electrical field. It is also desirable to provide a temperature-sensing element at each of the electrode locations, such as the illustrated thermocouples. Although thermocouples are shown, it shall be understood that other temperature elements may be used to sense or otherwise measure temperature such as RTDs, and others. With respect to control of each of the active electrical areas, it shall be understood that a controller can be used to measure temperature/energy applied at each of the conductive locations, as well as providing a visual indication as to how much energy has been applied over a period of time.

With respect to the distal tips of each of the different stimulation leads and disposable sheaths, it shall be understood that the distal tips may be active, electrical areas/electrodes. Thus, in addition to electrodes being selectively spaced along the length of the stimulation lead, the distal tips may also provide electrical or thermal energy to targeted tissue.

Based upon the foregoing, the invention provides a stimulation lead especially adapted for treatment of many types of ailments to include, disc ailments SI joint ailments, and other spine ailments to include treatment of structures that have large and diffuse innervations such as, but not limited to, the superior hypogastric plexus, sympathetic chain, ganglion impar, zygapophyseal joints, and others.

The various embodiments provide a treating physician with stimulation leads of various configurations, which optimizes a physician's ability to accurately position the stimulation lead, as well as to accurately direct electrical stimulation.

While the above description and drawings disclose and illustrate embodiments of the invention, it should be understood that the invention is not limited to these embodiments. It will be appreciated that other modifications and changes employing the principles of the invention, particularly considering the foregoing teachings, may be made. Therefore, by the appended claims, the applicant intends to cover such modifications and other embodiments.

What is claimed is:

1. An adjustable length tension sleeve device for an electrical or thermal stimulation device, comprising:
   a sleeve body having a plurality of legs, the body having a shape that changes lengths between a first relaxed state and a second stressed state, wherein the shape of the body lies substantially in a common plane to prevent induction of an electric current when the stimulation device is subjected to a magnetic field;
   a first end of the sleeve body terminating adjacent a proximal end of a stimulation lead or a proximal end of a lead extension of the stimulation device;
   a second end of the sleeve body extending a predetermined length along the stimulation lead and lead extension;
   at least one tab located at a selected one of the first or second ends of the sleeve body; and
   a line of weakness extending longitudinally along said sleeve body and communicating with said at least one tab.

2. A device, as claimed in claim 1, wherein:
said sleeve body further comprises a longitudinal axis extending between said first end and said second end of said body, a first straight leg offset from said axis by a first angle when said shape is in said first relaxed state, and said first straight leg is offset from said axis by a second angle when said shape is in said second stressed state, said first angle is different than said second angle.

3. A device, as claimed in claim 1, wherein:
said sleeve body further comprises a first curved leg having a first radius when said shape is in said first relaxed state, and said first curved leg having a second radius when said shape is in said second stressed state, said first radius is smaller than said second radius.

4. A device, as claimed in claim 1, wherein:
said shape of said sleeve body is not a coil.

5. An electrical or thermal stimulation device for treating tissue, said device comprising:
a stimulation lead having a first end, a second end, and at least one conducting wire disposed between the first end and the second end;
a plurality of electrodes positioned on the first end of the stimulation lead;
a lead extension positioned on the second end of the stimulation lead, the lead extension interconnected with a source of electrical energy, the electrodes communicating with the source of electrical energy for providing electrical or thermal stimulation of tissue proximate to the electrodes;
an adjustable length tension sleeve having a shape that changes lengths between a first relaxed state and a second stressed state, wherein the shape of the adjustable tension sleeve lies substantially in a common plane to prevent induction of an electric current when the stimulation device is subjected to a magnetic field, the adjustable length tension sleeve including (a) a plurality of legs (b) an internal passage for receiving the stimulation lead and lead extension, (c) at least one tab located at a selected end of the sleeve, and (d) a line of weakness extending longitudinally along said sleeve and communicating with said at least one tab.

6. A device, as claimed in claim 5, wherein:
said sleeve further comprises a longitudinal axis extending between a first end and a second end of said sleeve; and
a first straight leg of said plurality of legs being offset from said axis by a first angle when said shape is in said first relaxed state, and said first straight leg is offset from said axis by a second angle when said shape is in said second stressed state, said first angle is being different than said second angle.

7. A device, as claimed in claim 5, wherein:
said sleeve further comprises a first curved leg of said plurality of legs having a first radius when said shape is in said first relaxed state, and said first curved leg having a second radius when said shape is in said second stressed state, said first radius is smaller than said second radius.

8. A device, as claimed in claim 5, wherein:
said shape of said sleeve is not a coil.

9. A method of selectively changing a length of a tension sleeve used with an electrical or thermal stimulation device, the method comprising:
providing a stimulation lead having a first end, a second end, and at least one conducting wire disposed between the first end and the second end;
providing a plurality of electrodes positioned on the first end of the stimulation lead;
providing a lead extension positioned on the second end of the stimulation lead, the electrodes extending through the lead extension and communicating with a source of electrical energy to provide stimulation of tissue proximate to the electrodes;
providing an adjustable length tension sleeve mounted over said stimulation lead and lead extension, the adjustable length tension sleeve having a shape that changes between a first relaxed state and a second stressed state, wherein the adjustable length tension sleeve lies substantially in a common plane to prevent induction of an electric current when the stimulation device is subjected to a magnetic field, the adjustable length tension sleeve further having (a) a plurality of legs (b) at least one tab located at a selected end of the sleeve, and (c) a line of weakness extending longitudinally along said adjustable length sleeve and communicating with said at least one tab; and
activating the at least one tab to strip away a selected length of the adjustable length sleeve to thereby expose a corresponding length of the stimulation lead or lead extension.

10. A method, as claimed in claim 9, wherein:
said sleeve further comprises a longitudinal axis extending between a first end and a second end of said sleeve, a first straight leg of said plurality of legs being offset from said axis by a first angle when said shape is in said first relaxed state, and said first straight leg is offset from said axis by a second angle when said shape is in said second stressed state, said first angle is different than said second angle.

11. A method, as claimed in claim 9, wherein:
said sleeve further comprises a first curved leg of said plurality of legs having a first radius when said shape is in said first relaxed state, and said first curved leg having a second radius when said shape is in said second stressed state, said first radius is smaller than said second radius.

12. A device, as claimed in claim 9, wherein:
said shape of said sleeve is not a coil.

* * * * *